United States Patent
Matsui et al.

[11] Patent Number: 6,110,714
[45] Date of Patent: Aug. 29, 2000

[54] PROCESS FOR PRODUCING L-GLUTAMIC ACID BY FERMENTATION

[75] Inventors: Kazuhiko Matsui; Kumiko Fukase; Nobuharu Tsujimoto, all of Kawasaki, Japan

[73] Assignee: Ajinomoto Co., Inc., Tokyo, Japan

[21] Appl. No.: 09/011,479

[22] PCT Filed: Jul. 12, 1996

[86] PCT No.: PCT/JP96/01944

§ 371 Date: Feb. 20, 1998

§ 102(e) Date: Feb. 20, 1998

[87] PCT Pub. No.: WO97/08294

PCT Pub. Date: Mar. 6, 1997

[30] Foreign Application Priority Data

Aug. 23, 1995 [JP] Japan .................................. 7-214585

[51] Int. Cl.$^7$ ............... C12N 1/21; C12N 15/01; C12P 13/14

[52] U.S. Cl. ............... 435/110; 435/252.3; 435/252.8; 435/172.1

[58] Field of Search .................. 435/252.3, 252.5, 435/252.8, 110, 172.1

[56] References Cited

U.S. PATENT DOCUMENTS

| | | | |
|---|---|---|---|
| 4,411,991 | 10/1983 | Hirakawa et al. | 435/42 |
| 5,378,616 | 1/1995 | Tujimoto et al. | 435/110 |
| 5,393,671 | 2/1995 | Tujimoto et al. | 435/252.8 |
| 5,573,945 | 11/1996 | Ono et al. | 435/252.33 |
| 5,846,790 | 12/1998 | Kimura et al. | 435/110 |
| 5,908,768 | 6/1999 | Ono et al. | 435/110 |

OTHER PUBLICATIONS

Bates H, et al. "Spontaneous and UV–induced mutations in *Escherichia coli* K–12 strains with altered or absent DNA polymerase I." J Bacteriol., vol. 171(5):2480–4, Jun. 1989.

Jackson JH, et al. A mechanism for valine–resistant growth of *Escherichia coli* K–12 supported by the valine–sensitive acetohydroxy acid synthase IV activity from ilvJ662, Biochimie. 1993, vol. 75(9):759–65.

Quay SC, et al. Role of transport systems in amino acid metabolism: leucine toxicity and the branched–chain amino acid transport systems J Bacteriol. 1977, vol. 129(3):1257–65.

Herbert et al. J. Gen Microbiol, 1968, vol. 53, pp. 363–381, 1968.

Berberich, Biochem. Biophy Res Comm, 1972, vol. 47 pp. 1498–1503.

A. A. Herbert et al, Molec. Gen. Genetics, 1969, vol. 105, pp. 182–190.

Isamu Shiio et al, The Journal of Biochemistry, 1961, vol. 50, No. 2, pp. 164–165.

E. Vanderwinkel et al, Biochemical and Biophysical Research Communications, 1963, vol. 12, No. 2, pp. 157–162.

*Primary Examiner*—Ponnathapu Achutamurthy
*Assistant Examiner*—Bradley S. Mayhew
*Attorney, Agent, or Firm*—Oblon, Spivak, McClelland, Maier & Neustadt, P.C.

[57] ABSTRACT

An isolated mutant microorganism which belongs to the genus Escherichia, which exhibits valine sensitivity which is indicated by failure to grow in an M9 minimum growth medium containing 50 mg/liter of valine, and which has amplified citrate synthase activity and phosphoenolpyruvate carboxylase activity and which has L-glutamic acid-productivity.

6 Claims, 1 Drawing Sheet

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA, primer for amplification for Escherichia coli gltA
      gene

<400> SEQUENCE: 1
tctgttacct gcagacgtcg                                              20

<210> SEQ ID NO 2
<211> LENGTH: 20
```

```
<212> TYPE: DNA
<213> ORGANISM: Artificial Sequence
<220> FEATURE:
<223> OTHER INFORMATION: Description of Artificial Sequence:Synthetic
      DNA, primer for amplification of Escherichia coli gltA
      gene

<400> SEQUENCE: 2
aagtgaattc cgccagaacc                                           20
```

PROCESS FOR PRODUCING L-GLUTAMIC ACID BY FERMENTATION

This application is filed under 35 U.S.C. 371 as the National Stage of PCT/JP96/01944, filed Jul. 12, 1996.

TECHNICAL FIELD

The present invention relates to a process for producing L-glutamic acid by fermentation. L-glutamic acid is an important amino acid as food, pharmaceutical preparations or the like.

BACKGROUND ART

L-glutamic acid has been produced by fermentation mainly using so-called coryneform L-glutamic acid-producing strains belonging to the genus Brevibacterium, Corynebacterium or Microbacterium or mutants thereof (Amino-Acid Fermentation, Gakkai Shuppan Center, pp. 195–215, 1986). The other known methods of producing L-glutamic acid by fermentation use microorganisms belonging to the genus Bacillus, Streptomyces or Penicillium (U.S. Pat. No. 3,220,929), and microorganisms belonging to the genus Pseudomonas, Arthrobacter, Serratia or Candida (U.S. Pat. No. 3,563,857). The L-glutamic acid productivity is remarkably increased by the conventional methods. However, in order to meet foreseen increased needs in the future, the development of a more inexpensive and efficient method of producing L-glutamic acid has been in demand.

There is a possibility that bacteria of the genus Escherichia will be used as excellent L-glutamic acid producing-strains in the future because of its high growth rate and advanced gene analysis. It has only been reported so far that a mutant of wild type strain *Escherichia coli* W, results in accumulation of L-glutamic acid in small amounts of about 2.3 g/liter (J. Biochem., vol. 50, pp. 164–165, 1961). However, recently, it has been shown that a mutant of *Escherichia coli* K-12, in which α-ketoglutaric acid dehydrogenase (hereinafter abbreviated as "α-KGDH) activity is deficient or reduced, exhibits high L-glutamic acid productivity [Japanese Laid-Open Patent Application (Kokai) No. 244,970/1993]. Wild type strains belonging to the genus Escherichia include strains having properties which are better than those of *Escherichia coli* K-12 and mutants thereof. For Example, it has been reported that *Escherichia coli* B exhibits higher growth rate than *Escherichia coli* K-12 and mutants thereof and gives a high yield of biomass based on glucose consumed (J. Biotechnology, vol. 2, pp. 191–206, 1985; and Appl. Environ. Microbiol., vol. 56, pp. 1004–1011, 1990).

It is an object of the present invention to provide an inexpensive and efficient process for producing L-glutamic acid by propagating L-glutamic acid-producing strain which belongs to the genus Escherichia.

DISCLOSURE OF THE INVENTION

The present inventors have assiduously conducted investigations on a process for producing L-glutamic acid using bacteria of the genus Escherichia, and have consequently found that a strain obtained by amplifying citrate synthase (hereinafter abbreviated as "CS") activity and phosphoenolpyruvate carboxylase (hereinafter abbreviated as "PPC") activity in a valine-sensitive strain has high L-glutamic acid-productivity. This finding has led to the completion of the present invention.

That is, the present invention is as follows.

Invention 1. A microorganism which belongs to the genus Escherichia, which exhibits valine sensitivity, and which has amplified citrate synthase activity and phosphoenolpyruvate carboxylase activity and which has L-glutamic acid-productivity.

Invention 2. A microorganism according to the Invention 1, wherein α-ketoglutaric acid dehydrogenase activity is deficient or reduced.

Invention 3. A microorganism according to any of the Inventions 1 and 2, which belongs to *Escherichia coli*.

Invention 4. A microorganism according to the Invention 3, which belongs to *Escherichia coli* B strain.

Invention 5. A microorganism according to the Invention 3, which belongs to *Escherichia coli* K-12 strain.

Invention 6. A process for producing L-glutamic acid by fermentation, which comprises cultivating in a liquid medium a microorganism according to any of the Inventions 1 to 5, accumulating L-glutamic acid in the broth, and recovering said L-glutamic acid.

Figure 1:
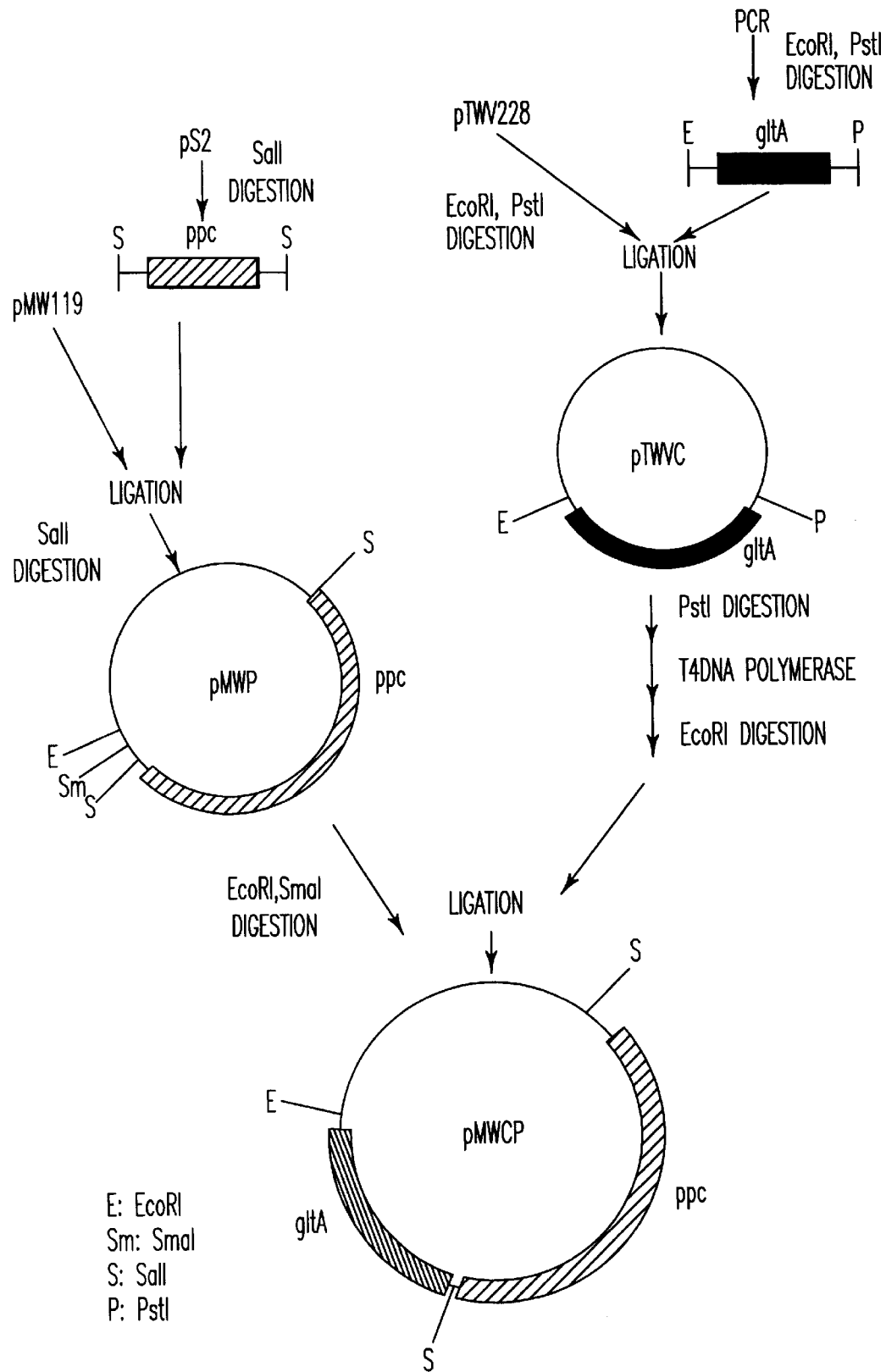
FIG. 1 is a view showing the construction of plasmid pMWCP.

BEST EMBODIMENT FOR CARRYING OUT THE INVENTION (1) Isolation of a valine-sensitive mutant In order to propagate the strain of the present invention, a valine-sensitive mutant is first isolated using as a parent strain a wild type strain which belongs to the genus Escherichia and exhibits valine resistance or its mutant. Specific examples of such a wild type strain are as follows.

*Escherichia coli* B (ATCC 11303)

*Escherichia coli* W (ATCC 9637)

The valine-sensitive mutant is isolated from the strain which belongs to the genus Escherichia and which exhibits valine resistance in the following manner.

First, the above-mentioned valine-resistant strain is mutated by a conventional method, for example, a method in which the strain is irradiated with X-rays or ultraviolet rays or is treated with a mutagen such as N-methyl-N'-nitro-N-nitrosoguanidine (hereinafter abbreviated as "NG").

Alternatively, the desired mutation can be introduced efficiently by a gene engineering method such as transduction, gene recombination or the like.

The valine-sensitive strain is obtained by transduction as follows. That is, *Escherichia coli* K-12 is known to show valine sensitivity (Amino Acid: Biosynthesis and Genetic Regulation, compiled by Klaus M. Herrman & Ronald L. Somerville, Addison-Wesley Publishing Company Inc., pp. 250–251, 1983). Therefore, valine sensitivity derived from *Escherichia coli* K-12 can be transduced into a valine-resistant strain using a phage lysate obtained by infecting *Escherichia coli* K-12 with P1 phage.

After the valine sensitivity has been introduced through mutation of the parent strain or transduction therein, the desired valine-sensitive strain can be isolated as a mutant which cannot grow on a valine-containing minimum medium or of which the growth rate is notably decreased.

A specific example of the thus-obtained valine-sensitive strain is *Escherichia coli* B11.

*Escherichia coli* B 11 is a valine-sensitive strain derived from *Escherichia coli* B through mutation. It is presumed that in this mutant, a metabolic pathway from pyruvic acid to valine is suppressed by the biosynthesis of valine, with the result that the pathway from pyruvic acid to acetyl CoA is improved.

It is not necessary to obtain a new strain which belongs to the genus Escherichia and has valine-sensitivity, if another strain having these characteristics is available. Examples of such strains include *Escherichia coli* K-12 strain, *Escherichia coli* W3110 strain and so on. *Escherichia coli* AJ12624 and *Escherichia coli* AJ12628 which are disclosed in Japanese Laid-open Patent Application (Kokai) No. 244,970/1993 are derived from *Escherichia coli* W3110 strain and have reduced or deficient α-KGDH activity. A strain in which α-KGDH activity is deficient or reduced has improved L-glutamic acid productivity and therefore is preferred as a microorganism of the present invention.

(2) Amplification of PPC activity and CS activity

In an Example to be described later, a strain which belongs to the genus Escherichia and which has amplified PPC activity and CS activity was obtained using, as a host, a valine-sensitive strain of the genus Escherichia. It is also possible to conduct propagation such that a strain having amplified PPC activity and CS activity is obtained using a valine-resistant strain of the genus Escherichia as a host and valine sensitivity is then conferred thereto.

Accordingly, as the host which is used to culture the strain having amplified PPC activity and CS activity, a mutant of the genus Escherichia to which valine sensitivity is conferred, a wild type strain of the genus Escherichia which has valine resistance, or a mutant thereof is used. Specific Examples of such a host are as follows.

*Escherichia coli* B11

*Escherichia coli* K-12 (ATCC 10798)

*Escherichia coli* B (ATCC 11303)

*Escherichia coli* W (ATCC 9637)

In order to amplify PPC activity and CS activity, genes encoding PPC and CS are cloned on an appropriate vector, and the above-mentioned host is transformed with the thus-obtained recombinant vector. Since the number of copies of the genes encoding PPC and CS (hereinafter abbreviated as "ppc gene" and "gltA gene" respectively) in the transformant is increased, PPC activity and CS activity are then amplified. Examples of the above mentioned vector include listed plasmid vectors, phage vectors, transposon vectors and so on.

The PPC gene and the gltA gene can be obtained by using mutants in which PPC activity or CS activity are deficient and isolating genes through which to complement their auxotrophies. Since the nucleotide sequences of these genes of *Escherichia coli* have already been reported (J. Biochem., vol. 95, pp. 909–916, 1984; and Biochemistry, vol. 22, pp. 5243 5249, 1983), it is also possible that primers are synthesized on the basis of the respective nucleotide sequences, and the genes are obtained by PCR using chromosomal DNAs as templates.

Any plasmid can be used for the gene cloning so long as it is replicable in bacteria of the genus Escherichia. Specific examples of plasmid include pBR322, pTWV228, pMW119 and pUC19.

The ppc gene and the gltA gene are introduced into the is above-mentioned starting parent strain as a host by being cloned on a single vector or by being cloned separately on two types co-existent vectors.

PPC activity and CS activity can be amplified by ligating the ppc gene and the gltA gene with a plasmid vector or plasmid vectors, introducing the obtained recombinant plasmid(s) into the above-mentioned host and keeping the plasmid(s) in the host. PPC activity and CS activity can also be amplified by causing additional copies of the ppc gene and the gltA gene to exist in the chromosomal DNA of the above-mentioned host. Additional copies of the ppc gene and the gltA gene are transduced into the chromosomal DNA of the microorganism of the genus Escherichia through homologous recombination using the sequences present in the chromosomal DNA as a target. Suitable such sequences of chromosomal DNA include a sequence which is present in multicopies is preferred and, for example, a repetitive DNA and an inverted repeat present at an end of an insertion sequence or a transposon can be used. Alternatively, as disclosed in Japanese Laid-Open Patent Application (Kokai) No. 109,985/1990, it is also possible to clone the ppc gene and the gltA gene on a transposon and then transpose this transposon into chromosomal DNA. In either method, the number of copies of the ppc gene and the gltA gene is increased within the transformant, and PPC activity and CS activity are consequently amplified.

Besides the above-mentioned gene amplification, PPC activity and CS activity can also be amplified by replacing the promoters of the ppc gene and the gltA gene with strong promoters. For example, a lac promoter, a trp promoter, a trc promoter, a tac promoter, a $P_R$ promoter, and a $P_L$ promoter of a λ phage are known to be strong promoters. The promoters of both genes are replaced with these promoters, with the result that the expression of the ppc gene and the gltA gene increases thereby amplifying PPC activity and CS activity.

It has been reported that L-glutamic acid productivity is improved by conferring a diminished ability to degrade L-glutamic acid and the constitutive expression of malate synthase-isocitrate lyase-isocitrate dehydrogenase kinase/phosphatase operon (hereinafter abbreviated as "ace operon") to a strain [Japanese Laid-Open Patent Application (Kokai) No. 244,970/1993]. It is easily presumed that when the L-glutamic acid-productive strain of the present invention has these properties, L-glutamic acid productivity is advantageously increased.

Needless-to-say, from the standpoint of improvement of L-glutamic acid productivity, it is advantageous that the L-glutamic acid-productive strain of the present invention has further auxotrophies, drug resistances, drug sensitivities and drug dependencies which are well-known so that it may be effective for improving the productivity of L-glutamic acid-productive strains.

(3) Production of L-glutamic acid using the strain of the present invention

Production of L-glutamic acid using a strain which belongs to the genus Escherichia, to which valine sensitivity is conferred and which has amplified PPC activity and CS activity can be conducted by a standard culture method in an ordinary nutrient medium containing a carbon source, a nitrogen source, inorganic salts and optionally an organic micronutrient such as an amino acid, a vitamin or the like. Any carbon source and nitrogen source may be used so long as these sources can be utilized in the strain to be cultured.

Examples of carbon sources include carbohydrates such as glucose, glycerol, fructose, sucrose, maltose, mannose, galactose, starch hydrolyzate and molasses. Further, organic acids such as acetic acid and citric acid can be used as a sole carbon source or in combination with other carbon sources.

Examples of nitrogen sources include ammonia, ammonium salts such as ammonium sulfate, ammonium carbonate, ammonium chloride and ammonium phosphate, and nitrates.

Examples of organic trace nutrients include amino acids, vitamins, fatty acids and nucleic acids as well as peptone, casamino acid, yeast extract and a soybean protein hydrolyzate containing the same. When using an auxotrophic mutant that requires an amino acid or the like for growth, a required nutrient has to be supplemented.

Examples of the inorganic salts include phosphate salts, magnesium salts, calcium salts, iron salts and manganese salts.

The cultivation is aerobically conducted at a fermentation temperature of from 20 to 45° C. while controlling the pH to the range from 5 to 9. When the pH is decreased during the cultivation, the pH is controlled with calcium carbonate or with an alkali such as ammonia gas. The cultivation is conducted in this manner for 10 hours to 4 days to accumulate a considerable amount of L-glutamic acid in the culture broth.

L-glutamic acid may be recovered from the culture broth at the end of the cultivation by a known method such as removing cells from the broth, and then concentration and crystallization or by ion-exchange chromatography.

EXAMPLE

The present invention will be illustrated more specifically by referring to the following Example.

(1) Isolation of a valine-sensitive mutant from *Escherichia coli* B

Five microliters of a cell suspension ($10^5$ cells/ml) of *Escherichia coli* B and W3110 derived from *Escherichia coli* K-12 were spotted on an M9 minimum agar medium (A Short Course In Bacterial Genetics, Cold Spring Harbor Laboratory Press, J. Miller, p.437, 1992) containing valine at various concentrations, and were incubated overnight at 37° C. The growth of the cells was then examined. As a result, *Escherichia coli* B grew on the M9 minimum medium containing 5 g/liter of valine, but *Escherichia coli* W3110 did not grow even in the M9 minimum medium containing 50 mg/liter of valine. By the way, both of the strains grew well on the valine-free M9 minimum medium.

Isolation of the mutant having the same valine-sensitivity as W3110 from *Escherichia coli* B.

*Escherichia coli* B was cultivated overnight at 37° C. in a 2YT liquid medium containing 16 g/liter of bacto tryptone, 10 g/liter of bacto yeast extract and 5 g/liter of NaCl (pH 7.2), then re-inoculated in the 2YT liquid medium, and cultivated at 37° C. The cells which were at the logarithmic growth phase were collected, washed with a 50 mM phosphate buffer (pH 6.0), suspended in the phosphate buffer containing 200 µg/ml of NG, and cultivated at 37° C. for 30 minutes. Thereafter, the cells were collected, and washed with the phosphate buffer. A part of the cells was inoculated into the 2YT liquid medium, and cultivated overnight at 37° C. Then the cells were collected, and washed with the phosphate buffer. An M9 minimum liquid medium containing 100 mg/liter of valine was inoculated with a part of the cells, and the cells were cultivated at 37° C. for 2 hours. Subsequently, penicillin was added in an amount of 200 units/ml, and was further cultivated overnight to concentrate the valine-sensitive mutant. Then, the culture was appropriately diluted, and the number of living cells was counted. The culture was diluted for a replica method on the basis of the number of living cells, spread on the M9 minimum agar medium, and cultivated overnight at 37° C. The colonies formed were transplanted onto M9 minimum agar medium containing 100 mg/liter of valine, and were cultivated overnight at 37° C. The strains considered to be valine-sensitive were strains which did not grow on the valine-containing medium, and which were isolated. After single colony isolation, the growth of these strains in the M9 minimum agar medium containing valine at various concentrations was examined. Consequently, the three valine-sensitive mutants were isolated which did not grow on the M9 minimum agar medium containing 50 mg/liter of valine.

*Escherichia coli* B and the thus-obtained three valine-sensitive strains were inoculated into 50-milliliter large test tubes each containing 5 ml of a medium having a composition shown in Table 1, and were cultivated with reciprocal shaker (115 rpm) until the glucose in the medium were consumed at 37° C. At the end of cultivation, the amount of L-glutamic acid accumulated in the supernatant of the culture was measured through a Biotech Analyzer manufactured by Asahi Chemical Industry Co., Ltd. As a result, none of *Escherichia coli* B and the three valine-sensitive strains accumulated L-glutamic acid in the broth. Meanwhile, the accumulation of valine in the supernatant of each culture was examined through thin-layer chromatography and its reaction with ninhydrin. A valine spot was slightly observed in *Escherichia coli* B, but no valine spot was observed in the valine-sensitive strains.

The typical strain of the valine-sensitive strains isolated is designated as *Escherichia coli* 11.

TABLE 1

| Ingredients | Concentration (g/liter) |
| --- | --- |
| glucose | 40 |
| $(NH_4)_2SO_4$ | 20 |
| $KH_2PO_4$ | 1 |
| $MgSO_4 \cdot 7H_2O$ | 1 |
| $FeSO_4 \cdot 7H_2O$ | 0.01 |
| $MnSO_4 \cdot 5H_2O$ | 0.01 |
| yeast extract | 2 |
| thiamine hydrochloride | 0.01 |
| $CaCO_3$ | 20 |

(2) Cloning of the gltA gene of *Escherichia coli* W3110

The nucleotide sequence of the gltA gene of *Escherichia coli* has already been reported (Biochemistry, vol. 22, pp. 5243–5249, 1983). Primers of Sequence Nos. 1 and 2 of Sequence Table were synthesized on the basis of the nucleotide sequence reported, and the gltA gene was amplified by PCR using a chromosomal DNA of *Escherichia coli* W3110 as a template.

Sequence No. 1 of the primers synthesized corresponds to the sequence from the -342nd base to the -323rd base of the nucleotide sequence table of the gltA gene described in Biochemistry, vol. 22, p. 5246, 1983, provided that the -331st base G is replaced with C and a recognition sequence of restriction endonuclease PstI is inserted therein. Sequence No. 2 thereof corresponds to the sequence from the 2060th base to the 2079th base of the nucleotide sequence table of the gltA gene described in Biochemistry, vol. 22, p. 5247, 1983, provided that the 2070th base A is replaced with G and a recognition sequence of restriction endonuclease EcoRI is inserted therein. In the nucleotide sequence represented by Sequence No. 2, the reverse strand of the nucleotide sequence from the 2060th base to the 2079th base indicated in Biochemistry, vol. 22, p. 5247, 1983 is described from the 5'-side.

The chromosomal DNA of *Escherichia coli* W3110 was prepared by a standard method (Seibutsu Kohgaku Zikkensho, compiled by Society for Fermentation and Bioengineering, Japan, pp. 97–98, Baifukan, 1992). In PCR, the standard reaction conditions described in PCR Technology, compiled by Henry A. Ehlich, Stockton Press, 1989 were used.

The PCR product was purified by a standard method, and was then digested with restriction endonucleases PstI and EcoRI. The fragment was ligated with pTWV228 (purchased from Takara Shuzo) which had been digested with PstI and EcoRI using a ligation kit (purchased from Takara Shuzo). A competent cell (purchased from Takara Shuzo) of *Escherichia coli* JM1 09 was transformed with the thus-obtained ligation product, and was spread on an L medium (pH 7.2) containing 10 g/liter of bacto tryptone, 5 g/liter of bacto yeast extract, 5 g/liter of NaCl, 15 g/liter of agar, 10 μg/ml of IPTG (isopropyl-β-D-thiogalactopyranoside), 40 μg/ml of X-Gal-(5-bromo-4-chloro-3-indole-β-D-galactoside) and 100 μg/ml of ampicillin, and was cultivated overnight. Then, the white colonies which appeared were lifted up.

A plasmid was prepared from the transformant strain by the alkali method (Seibutsu Kohgaku Zikken-sho, compiled by Society for Fermentation and Bioengineering, Japan, p. 105, Baifukan, 1992). Then, the restriction endonuclease map of the DNA fragment inserted into the vector was constructed, and compared with the restriction endonuclease map of the gltA gene reported. The plasmid having inserted therein the DNA fragment having the same restriction endonuclease map is designated as pTWVC.

Further, in order to confirm whether the gltA gene is expressed, pTWVC was introduced into a competent cell of gltA-deficient strain ME8330 (gltA6, fur::Tn5, galK30, pyrD36, relA1, rpsL129, thi-1, supE44, λ⁻) which had been prepared by the rubidium chloride method (Saishin Nohgaku Zikken no kiso, compiled by Tohoku University, Agricultural Department, Soft Science K.K., p. 157, 1990). The auxotrophy of the transformant obtained was checked, and it was ascertained that PTWVC supplemented gltA6 of ME8330. This ME8330 was obtained from National Institute of Gentics, Genetic Stock Research Center. ME8330 deficient in gltA requires L-glutamic acid for its growth and can be grown in the M9 minimum medium containing thiamine, uracil and L-glutamic acid.

CS activity of W3110, gltA-deficient ME8330 and pTWVC-containing ME8330 was measured by the method of Weitzman et al. (Methods in Enzymology, vol. 13, pp. 22 26, 1969). Consequently, as shown in Table 2, ME8330 did not have CS activity. Meanwhile, pTWVC-containing ME8330 exhibited CS activity which was approximately 4 times as high as wild type strain W3110.

TABLE 2

| Strain | CS activity (units/mg · protein) |
|---|---|
| W3110 | 0.69 |
| ME8330 | 0 |
| ME8330/pTWVC | 2.71 |

(3) Construction of a plasmid having ppc gene and gltA gene

The construction of plasmid pMWCP containing ppc gene and gltA gene is shown in FIG. 1.

First, plasmid pS2 in which a SalI fragment of 4.4 kb containing the whole region of ppc gene derived from *Escherichia coli* K-12 had been inserted into the SalI site of pBR322 (J. Biochem., vol. 95, pp. 909–916, 1984) was digested with SalI. The SalI fragment of 4.4 kb containing ppc gene was prepared through agarose gel electrophoresis, and was inserted into the SalI site of pMW119 (purchased from Nippon Gene). This plasmid is designated as pMWP. On the other hand, pTWVC having gltA gene was digested with PstI, and both termini thereof were changed into blunt-ended termini. This fragment was further digested with EcoRI. The thus-obtained DNA -fragment was mixed with pMWP digested with SmaI and EcoRI, and the mixture was subjected to ligation. ME8330 was transformed with the thus-ligated DNA sample, and an ampicillin-resistant transformant strain which lost L-glutamic acid auxotrophy were selected. A plasmid was prepared from this strain, and ME8330 was re-transformed with this plasmid. It was identified that the transformant lost L-glutamic acid auxotrophy. Further, the restriction endonuclease map was prepared, and it was confirmed that ppc gene and gltA gene were present in this plasmid. This plasmid is designated as pMWCP. The transformation was conducted by the rubidium chloride method.

(4) Introduction of pMWCP into *Escherichia coli* B and valine-sensitive mutant B and valine-sensitive mutant B11 and evaluation of culture

*Escherichia coli* B and valine-sensitive B11 thereof were transformed with plasmid pMWCP by the rubidium chloride method. Three transformants of each type obtained independently was inoculated in a 50-milliliter large test tube containing 5 ml of a medium having a composition shown in Table 1, and was cultivated at 37° C. with reciprocal shaker until glucose in the medium was consumed. Furthermore, transformants, B11 transformed with pMWP or pMWC were also subjected to above-mentioned cultivation. pMWC was constructed by ligating a gltA gene-containing PstI-EcoRI fragment prepared from pTWVC with pMW119 digested with PstI and EcoRI. In the cultivation of the transformants, 100 μg/ml of ampicillin were added to retain the plasmid stably.

At the end of the cultivation, the amount of L-glutamic acid accumulated in the culture broth was measured, and the results are shown in Table 3. In the results of the cultivation of the transformants, the amount of L-glutamic acid was indicated in terms of the average value of that of three transformants. In the strain which was obtained using the valine-resistant *Escherichia coli* B as a host and which had amplified CS activity and PPC activity, L-glutamic acid had not accumulated. Whereas, in the strain which was obtained using valine-sensitive B11 as a host and which had amplified CS activity and PCC activity, a considerable amount of L-glutamic acid had accumulated. In the strain which was obtained by introducing pMWP into B11 and which had amplified PPC activity alone, L-glutamic acid had not accumulated. Whereas, in the strain which was obtained by introducing pMWC into B11 and which had amplified CS activity alone, L-glutamic acid had accumulated, but the amount of L-glutamic acid accumulated in this strain was less than that of L-glutamic acid accumulated in the strain having both of amplified CS activity and PPC activity.

TABLE 3

| Strain | Property of a host | Amount of L-glutamic acid accumulated (g/liter) |
|---|---|---|
| B/pMWCP | valine resistance | 0 |
| B11/pMWCP | valine sensitivity | 9.8 |
| B11/pMWPC | valine sensitivity | 0 |
| B11/pMWC | valine sensitivity | 3.6 |

From the above-mentioned results, it was found that the combination of the valine-sensitive mutation and the amplification of CS activity and PPC activity was indispensable to propagate the L-glutamic acid-producing strain from a valine-resistant wild type strain such as *Escherichia coli* B. The strain obtained by introducing plasmid pMWCP having the gltA gene and the ppc gene into B11 is designated AJ13138.

A valine-sensitive mutant B11 of *Escherichia coli* B is obtained by curing the plasmid from AJ13138 deposited without damaging the host cells. The plasmid is naturally lost at times or can be cured (Bact. Rev., vol. 36, pp. 361–405, 1972). In the curing procedure of the plasmid, AJ13138 is cultivated in an L-broth overnight at 40° C. Then, the culture is appropriately diluted, and spread on an ampicillin-free L-medium. After the culture is incubated overnight at 37° C., the colonies formed are transplanted into an L-medium containing 100 μg/ml of ampicillin, and then the ampicillin-sensitive colonies are isolated. The thus-obtained ampicillin-sensitive strain is B11.

(5) Introduction of pMWCP into *Escherichia coli* K-12 and evaluation of culture

*Escherichia coli* W3110sucA::Km$^r$ was transformed with plasmid pMWP, pMWC and pMWCP by the rubidium chloride method to obtain three types of transformants. Four transformants of each type obtained independently were inoculated in a 500-milliliter large Sakaguchi flask containing 20 ml of a medium having the composition shown in Table 4, and was cultivated at 37° C. in a reciprocal shaker for 25 hours until glucose in the medium was consumed. In the cultivation of the transformants, 100 μg/ml of ampicillin were added in order to stably retain the plasmid. *Escherichia coli* W3110sucA::Km$^1$ is disclosed in the Published European Patent Application 0 670 370 and is deficient in its α-KGDH because of the destruction of sucA gene.

TABLE 4

| Ingredients | Concentration (g/liter) |
| --- | --- |
| glucose | 20 |
| (NH$_4$)$_2$SO$_4$ | 20 |
| KH$_2$PO$_4$ | 1 |
| MgSO$_4$.7H$_2$O | 1 |
| FeSO$_4$.7H$_2$O | 0.01 |
| MnSO$_4$.5H$_2$O | 0.01 |
| yeast extract | 2 |
| thiamine hydrochloride | 0.01 |
| CaCO$_3$ | 3 |

At the end of the cultivation, the amount of L-glutamic acid which had accumulated in the culture broth was measured for each of the transformants, and the results are shown in Table 5. The amount of L-glutamic acid for each transformant is indicated in terms of average values. The greatest yield of L-glutamic acid was that obtained using the α-KGDH deficient strain derived from valine-sensitive *Escherichia coli* K-12 as a host and which had amplified CS activity and PPC activity.

TABLE 5

| Strain | Yield of L-glutamic acid accumulated (%) |
| --- | --- |
| W3110sucA::Km$^r$ | 41.1 |
| W3110sucA::Km$^r$/pMWP | 42.3 |
| W3110sucA::Km$^r$/pMWC | 44.5 |
| W3110sucA::Km$^r$/pMWCP | 47.3 |

Industrial Applicability

In accordance with the process of the present invention, L-glutamic acid productivity of a valine-resistant wild type strain which belongs to the genus Escherichia can be increased, and L-glutamic acid can be produced efficiently at low cost.

*Escherichia coli* AJ12624 was listed as deposited at the National Institute of Bioscience and Human Technology of the Agency of Industrial Science and Technology (1-3, Higashi 1 Chome Tsukuba-shi Ibaraki-ken 305, Japan) on Jul. 24, 1991 under deposit No. FERM P-12379. The strain was transferred to the international deposit under the Budapest Treaty on May 15, 1992 and given the accession number FERM BP-3853.

*Escherichia coli* AJ12628 was listed as deposited at the National Institute of Bioscience and Human Technology of the Agency of Industrial Science and Technology (1-3, Higashi 1 Chome Tsukuba-shi Ibaraki-ken 305, Japan) on Jul. 24, 1991 under deposit No. FEPM P-12380. The strain was transferred to the international deposit under the Budapest Treaty on May 15, 1992 and given the accession number FERM BP-3854.

*Escherichia coli* AJ13138 was listed as deposited at the National Institute of Bioscience and Human Technology of the Agency of Industrial Science and Technology (1-3, Higashi 1 Chome Tsukuba-shi Ibaraki-ken 305, Japan) on Aug. 17, 1995 under deposit No. FERM P-15115. The strain was transferred to the international deposit under the Budapest Treaty on Jun. 7, 1996 and given the accession number FERM BP-5565.

What is claimed is:

1. An isolated mutant microorganism which belongs to the genus Escherichia, which exhibits valine sensitivity, which is indicated by failure to grow in an M9 minimum growth medium containing 50 mg/liter of valine, and which has amplified citrate synthase activity and phosphoenolpyruvate carboxylase activity and which has L-glutamic acid-productivity.

2. The isolated mutant microorganism according to the claim 1, wherein α-ketoglutaric acid dehydrogenase activity is deficient or reduced.

3. The isolated mutant microorganism according to claim 1, which belongs to *Escherichia coli*.

4. The isolated microorganism according to the claim 3, which belongs to *Escherichia coli* B strain.

5. The isolated mutant microorganism according to the claim 3, which belongs to *Escherichia coli* K-12 strain.

6. A process for producing L-glutamic acid by fermentation, which comprises cultivating in a liquid medium a microorganism according to claim 1, accumulating L-glutamic acid in the broth, and recovering said L-glutamic acid.

* * * * *